United States Patent
Niitsu et al.

(10) Patent No.: US 6,268,336 B1
(45) Date of Patent: Jul. 31, 2001

(54) PHARMACEUTICAL COMPOSITION FOR TREATMENT OF HEPATIC DISEASES

(75) Inventors: Yoshiro Niitsu; Junji Kato, both of Hokkaido; Masato Higuchi, Shizuoka, all of (JP)

(73) Assignee: Chugai Seiyaku Kabushiki Kaisha (JP)

( * ) Notice: Subject to any disclaimer, the term of this patent is extended or adjusted under 35 U.S.C. 154(b) by 0 days.

(21) Appl. No.: 09/202,614

(22) PCT Filed: Jun. 13, 1997

(86) PCT No.: PCT/JP97/02054

§ 371 Date: Dec. 18, 1998

§ 102(e) Date: Dec. 18, 1998

(87) PCT Pub. No.: WO97/48411

PCT Pub. Date: Dec. 24, 1997

(30) Foreign Application Priority Data

Jun. 20, 1996 (JP) .................................................... 8-160320

(51) Int. Cl.$^7$ ........................... A61K 38/16; C01B 17/74; C01B 17/02
(52) U.S. Cl. ................................ 514/8; 424/529; 424/569
(58) Field of Search ................................ 514/8; 424/529, 424/569

(56) References Cited

U.S. PATENT DOCUMENTS 5,013,718   5/1991   Adamson et al. ........................ 514/8

FOREIGN PATENT DOCUMENTS 63-159322   7/1988   (JP) .
1-44317     9/1989   (JP) .
2-17156     4/1990   (JP) .
6-92316  *  11/1994  (JP) ............................... A61K/37/24

OTHER PUBLICATIONS

I.S. Trowbridge et al., "Human Cell Surface Glycoprotein Related to Cell Proliferation is the Receptor for Transferrin", Proc. Natl. Acad. Sci. USA, vol. 78, pp. 3039–3043, 1981.

Yutaka Kohgo et al., "Receptor Medicated Endocytosis Transferrin–Neocarzinostatin: Anti-tumor Effect of Transferrin–Neocarzinostatin Conjugate Which is Taken up by Cells with Receptor Medicated Endocytosis", J. Jpn. Soc. Cancer Ther., vol. 21(3), pp. 641–646 (1986).

Masato Higuchi et al., "Role of Sugar Chains in the Expression of the Biological Activity of Human Erythropoietin", The Journal of Biological Chemistry, vol. 267, No. 11, pp. 7703–7709, 1992.

Yukio Nakamura et al., "A Truncated Erythropoietin Receptor that Fails to Prevent Programmed Cell Death of Erythroid Cells", Science, vol. 257, pp. 1138–1141, 1992.

Pamela J. Fraker et al., Jr., "Protein and Cell Membrane Iodinations with a Sparingly Soluble Chloroamide, 1,3,4,6–Tetrachloro–3a, 6a–Diphenylglycoluril", Biochemical Biophysical Research Communications, vol. 80, No. 4, pp. 849–857, 1978.

D. K. Kelleher et al., "The Effect of Erythropoietin on Tumor Oxygenation in Normal and Anemic Rats", *Oxygen Transport to Tissue XV*, Adv. Exp. Med. Biol., vol. 345, pp. 517–524, 1994.

Mitchitami Yano, Strides in Medicine, vol. 171 (14), pp. 1079–1082, 1994. (Japanese).

Shiro Iino et al., "Interferon Treatment in Hepatitis C Virus Infection", Saishin Igaku, vol. 48, 12, pp. 2255–2261 (1993).

Masayoshi Kobune et al., "Role of Copper and Iron Ions on Development of Liver Injury in LEC rats", Lecture Summary of the 53$^{rd}$ Meeting of Japanese Cancer Society, p. 91 (1994).

Takigawa et al., Summary Collection of the 27$^{th}$ Western Sectional Meeting of Japanese Hepatic Society, vol. 33, Suppl. (2), p. 49, (1992).

Merck Manual, 16$^{th}$ Edition, Japanese Ed., 3$^{rd}$ printing (1995), Chapter 69, pp. 861–870, "Hepatitis".

Takigawa et al, 27$^{th}$ Western Sectional Meeting of Japanese Hepatic Soc. vol. 33, Suppl. (2) p 49, 1992.*

Kofume et al, Lecture Series of 53rd Meeting of Japanese Cancer Society p 91, 1994.*

Anagnostou et al 88CA: 45417, 1977.*

* cited by examiner

*Primary Examiner*—Russell Travers
(74) *Attorney, Agent, or Firm*—Finnegan, Henderson, Farabow, Garrett & Dunner, L.L.P.

(57) ABSTRACT

The present invention relates to a pharmaceutical composition for treatment of hepatic diseases which comprises erythropoietin as an active ingredient to reduce excess iron ions in the liver of a mammal with hepatic diseases, thus improving hepatic functions of said mammal. According to the present pharmaceutical composition with erythropoietin as an active ingredient, excess iron ions in the liver of a mammal with hepatic diseases can be decreased, so it is effective for treatment of chronic hepatitis, hepatic carcinoma, hepatocirrhosis etc. due to excess iron ions. Further, patient's anemia accompanying venesection can be prevented while excretion of excess iron ions can be promoted by using the venesection therapy in combination with the administration of said pharmaceutical composition. Furthermore, the pharmaceutical composition of the present invention is administered into a patient with chronic hepatitis C for whom IFN therapy is not effective to improve hepatic functions after which conventional IFN therapy is conducted whereby its therapeutic effect on said hepatitis can be expected.

6 Claims, 6 Drawing Sheets

PHARMACEUTICAL COMPOSITION FOR TREATMENT OF HEPATIC DISEASES

This application is a 371 of PCT/JP92/02054, filed Jun. 13, 1992, which priority Japan Appl. 160320/1996 filed Jun. 20, 1996.

TECHNICAL FIELD

The present invention relates to a pharmaceutical composition for treatment of hepatic diseases which comprises erythropoietin as an active ingredient. In particular, the present invention relates to a pharmaceutical composition for treatment of hepatic diseases in which excess iron ions in the liver, considered to be closely related to hepatic diseases such as chronic hepatitis, hepatic carcinoma and hepatocirrhosis, are removed from hepatocytes preferably by use of venesection therapy in combination and reduced thereby improving hepatic functions.

BACKGROUND ART

Chronic hepatitis is a severe hepatic disease which forms hepatocirrhosis and hepatic carcinoma. Most cases of chronic hepatitis are caused by infection with hepatitis C virus (HCV). Interferon (IFN) therapy presently is used to treat chronic hepatitis C. Although its severe side effects are known, long-term administration of IFN for 4 to 6 months is necessary and has limited therapeutic effect. For example, studies of the effect of IFN therapy and of the properties of HCV, report that IFN therapy has a significant effect on the type III genotype virus (10 to 20% prevalence in Japan) but has only 20 to 30% effectiveness against the type II genotype virus, which represents at least 70% of the virus in Japan [Iino et al., Saishin Igaku, 99, 2225 (1993)]. Accordingly, there is a need for a new therapy for the latter patients for whom IFN therapy is not effective.

The inventors studied the mechanism of the onset of hepatic disorders, using the LEC rat as a model animal with human hepatic carcinoma generated from chronic hepatitis. These studies revealed that feeding an LEC rat with conventional feed having metallic ions such as copper, iron etc. stimulated a rapid increase in hepatic copper as well as an increase in hepatic iron levels, thus causing a high incidence of severe hepatitis. On the other hand, feeding an iron-deficient feed caused only a slight increase in hepatic iron, and no observable severe hepatitis, although hepatic copper levels rapidly increased in a similar manner to the case of feeding with conventional feed. From these results, indicated that the major factor causing hepatic disorders is an abnormal increase of iron ions in the liver [Kofune et. al., Lecture Summary of the 53rd Meeting of Japanese Cancer Society, page 91, 1994]. Actually, chronic active hepatitis C can subside by removing iron ions through venesection [Takigawa et al., Summary Collection of the 27th western Sectional Meeting of Japanese Hepatic Society, Vol. 33, Supple (2), page 49, 1992] and a non-IFN responsive hepatitis can be changed into IFN responsive hepatitis through venesection [Hayashi et al., Igaku To Yakugaku, 29, 1487 (1993)]. However, although rapid venesection effectively reduces hepatic iron levels, it causes anemia. This anemia makes continued treatment difficult due to worsening of general conditions of the patient. Furthermore, when venesection is conducted to limit anemia in the patient, a long period of 1 or 2 years is required to obtain a sufficient therapeutic effect. During this long time period, however, chronic hepatitis often is transformed through hepatocirrhosis into hepatic carcinoma. Accordingly, there is a strong demand to develop therapies to improve hepatic functions as rapidly as possible.

It is further reported that one of antigens as cancer markers is a transferring receptor [Trowbridge, I. S. and Omary, M. B., Proc. Natl. Acad. Sci. USA, 78, 3039–3043 (1981)]. Some of the present inventors have reported that transferrin receptors occur abundantly in actively proliferating cancer cells, and that the presence of these transferrin receptors indicates the ability of cells to proliferate, or the malignancy of cancer cells [J. Jpn. Cancer Ther. 21(3), 641–646, Apr. (1986)]. Thus, so it is reasoned that a high iron ion concentration is required for cancer cells to actively proliferate.

Meanwhile, erythropoietin administration is proposed to treat a blood pigment symptom caused by blood-transfusion for improvement of chronic anemia resulting from renal functional disorders. In this case, erythropoietin is administered into anemic patients undergoing hemodialysis before their stored iron and serum iron are decreased as a result of venesection (Japanese Patent Publication No. 92316/1994). However, no report clarifies whether the hepatic functions of patients suffering hepatic disease such as chronic hepatitis or hepatic carcinoma are improved by erythropoietin administration.

Accordingly, the object of the present invention is to clarify the relationship between hepatic iron metabolism and erythropoietin to improve thereby and shorten treatment time. Another object is to provide a pharmaceutical composition for treatment of hepatic diseases which comprises erythropoietin as an active ingredient.

DISCLOSURE OF THE INVENTION

As a result of studies to solve the above-described problems, the present inventors discovered that erythropoietin promotes releasing of excess iron ions from the liver via specific receptors. This release decreases excess iron ions in the liver and thereby improves the hepatic functions of patients that have hepatic diseases such as chronic hepatitis, hepatic carcinoma and hepatocirrhosis. Furthermore, the present inventors discovered that venesection therapy can be combined with erythropoietin administration, to safely improve hepatic function in a short time without incurring excessive anemia. The inventors also discovered that the growth of transformed hepatocytes can be inhibited by erythropoietin.

The present invention relates to a pharmaceutical preparation for treatment of hepatic diseases which comprises erythropoietin as an active ingredient to reduce excess iron ions in the liver of a mammal with hepatic diseases, thus improving hepatic functions of said mammal.

BEST MODE FOR CARRYING OUT THE INVENTION

Figure 1:
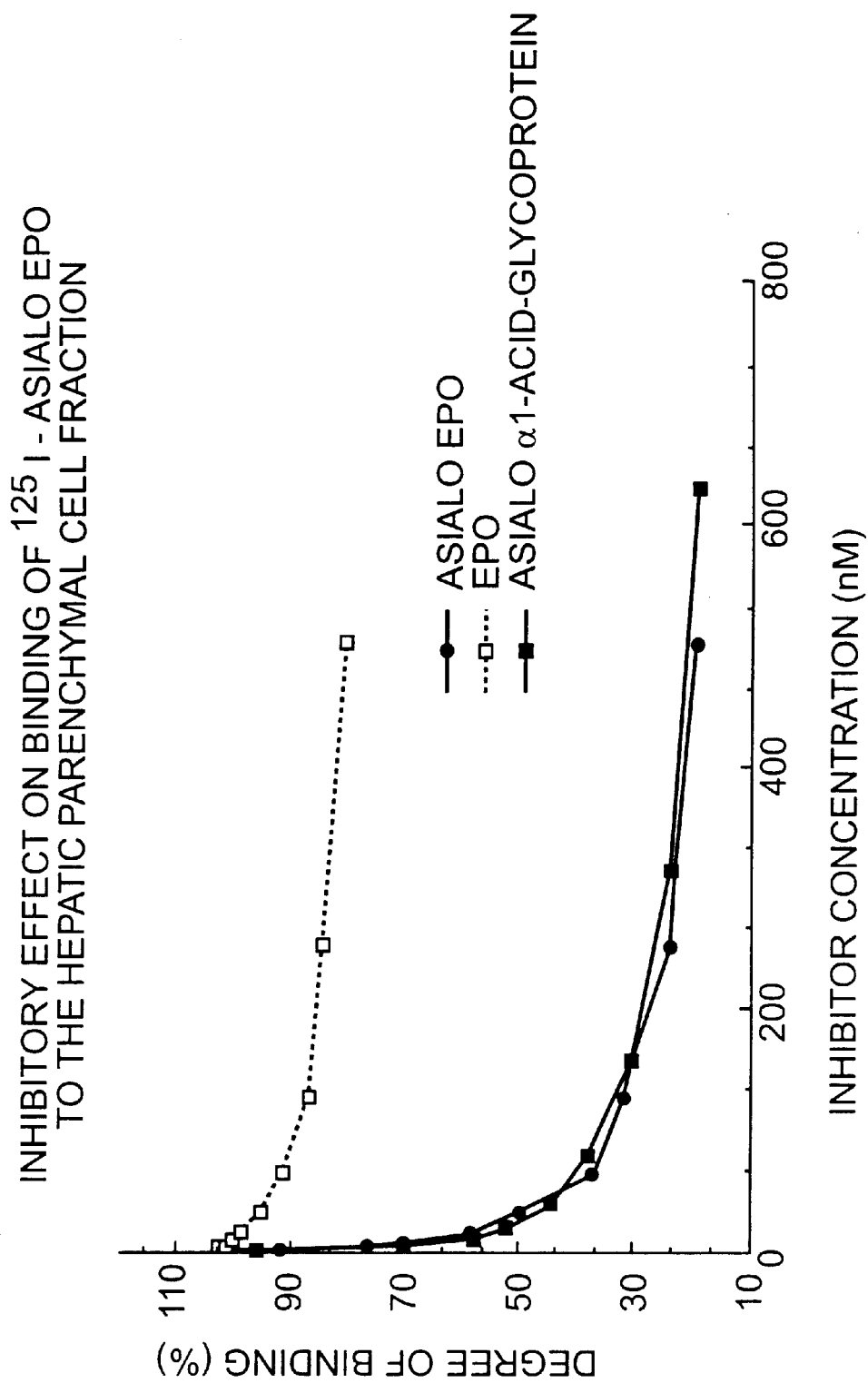
FIG. 1 is a graph where the inhibitory effects of asialo EPO, EPO, and asialo α1-acid-glycoprotein on the binding of $^{125}$I-asialo EPO to a hepatic parenchymal cell (AMLC) fraction were measured.

Hereinafter, the present invention is described in detail.

Erythropoietin, which is the active ingredient in the pharmaceutical composition of the present invention, is a glycoprotein with an apparent molecular weight of about 36,000 daltons. Erythropoietin causes erythroblast precursor cells to differentiate into erythrocytes. Various kinds of known erythropoietin such as natural erythropoietin purified from human urine etc., recombinant erythropoietin obtained by genetic engineering means and modified erythropoietin are active in this context (Japanese Patent Publication Nos. 44,317/1989, 17,156/1990 etc.)

For use in a pharmaceutical composition, the above-described erythropoietin may be dissolved along in physiological saline alone etc., but usually is dissolved along with other protein such as human serum albumin, gelatin etc., and/or sugar, such as mannitol, sorbitol etc. in physiological saline. In particular, erythropoietin is dissolved preferably with 0.01 to 0.1% by weight of human serum albumin and 1 to 1.5% by weight of D-mannitol in physiological saline.

Pharmaceutically acceptable stabilizers, regulators for pH, osmotic pressure etc. may be suitably added to the above physiological saline.

Although the dose of the pharmaceutical composition of the present invention shall be varied depending on the severity of symptoms, the age, weight etc. of a mammal as the subject of treatment, a therapeutically effective amount of erythropoietin as the active ingredient can be in the range of 10 to 10,000 U/kg of body weight for recombinant erythropoietin. If the venesection therapy described below is used in combination, erythropoietin is administered in the range of 10 to 2,000 U/kg of body weight.

In the present invention, production of erythrocytes is promoted by administration of erythropoietin, so blood removal such as venesection therapy is preferably used in combination to remove excess erythrocytes. The venesection therapy involves e.g. drawing about 200 ml blood from a patient with hepatitis, hepatic carcinoma, hepatocirrhosis or other hepatic diseases prior to administration of the pharmaceutical composition of the present invention. By this method, patient's anemia accompanying venesection can be prevented while excretion of excess iron ions from hepatocytes can be promoted.

A disease which can be treated by the pharmaceutical composition of the present invention includes hepatic diseases considered to be caused by excess iron ions in hepatocytes, for example, chronic hepatitis, hepatic carcinoma, and hepatocirrhosis etc. Chronic hepatitis is mostly due to infection with hepatitis C virus and includes chronic hepatitis C, severe chronic hepatitis C etc.

Hereinafter, the present invention is described with reference to Test Examples and Examples, which however are not intended to limit the present invention.

[Test Example 1]

Measurement of the ability of erythropoietin (EPO) to bind to hepatic cells $^{125}$I-EPO prepared according to the Indogen method [Franker, P. J. and Speck, J. C. Jr., Biochem. Biophys. Res. Commun. 80, 849–857 (1978)], and $^{125}$I-asialo EPO obtained by treatment of $^{125}$I-EPO at 80° C. for 60 minutes in the presence of 0.05 N hydrochloric acid, were measured for their ability to bind to the surfaces of hepatic parenchymal cells. The measurement of their binding ability was effected according to a method known in the art [Higuchi, M. et al., J. Biol. Chem., 267, 7703–7709 (1992)].

First, 0.5 nM $^{125}$I-asialo EPO was added to a mouse hepatic parenchymal cell (AMLC) fraction obtained by collagenase perfusion, and the inhibitory effects of asialo EPO, EPO, and asialo α1-acid-glycoprotein on the binding of $^{125}$I-asialo EPO to the hepatic parenchymal cell fraction were determined. The results are shown in FIG. 1. From FIG. 1, it was found that $^{125}$I-asialo EPO binds to the hepatic parenchymal cell fraction. It was further found that asialo EPO and asialo α1-acid-glycoprotein inhibit the binding of $^{125}$I-asialo EPO to an almost similar degree whereas EPO does not have a significant inhibitory effect on the binding. This result indicates that $^{125}$I-asialo EPO binds to the hepatic parenchymal cell fraction not via EPO receptors but via asialo glycoprotein receptors.

Figure 2:
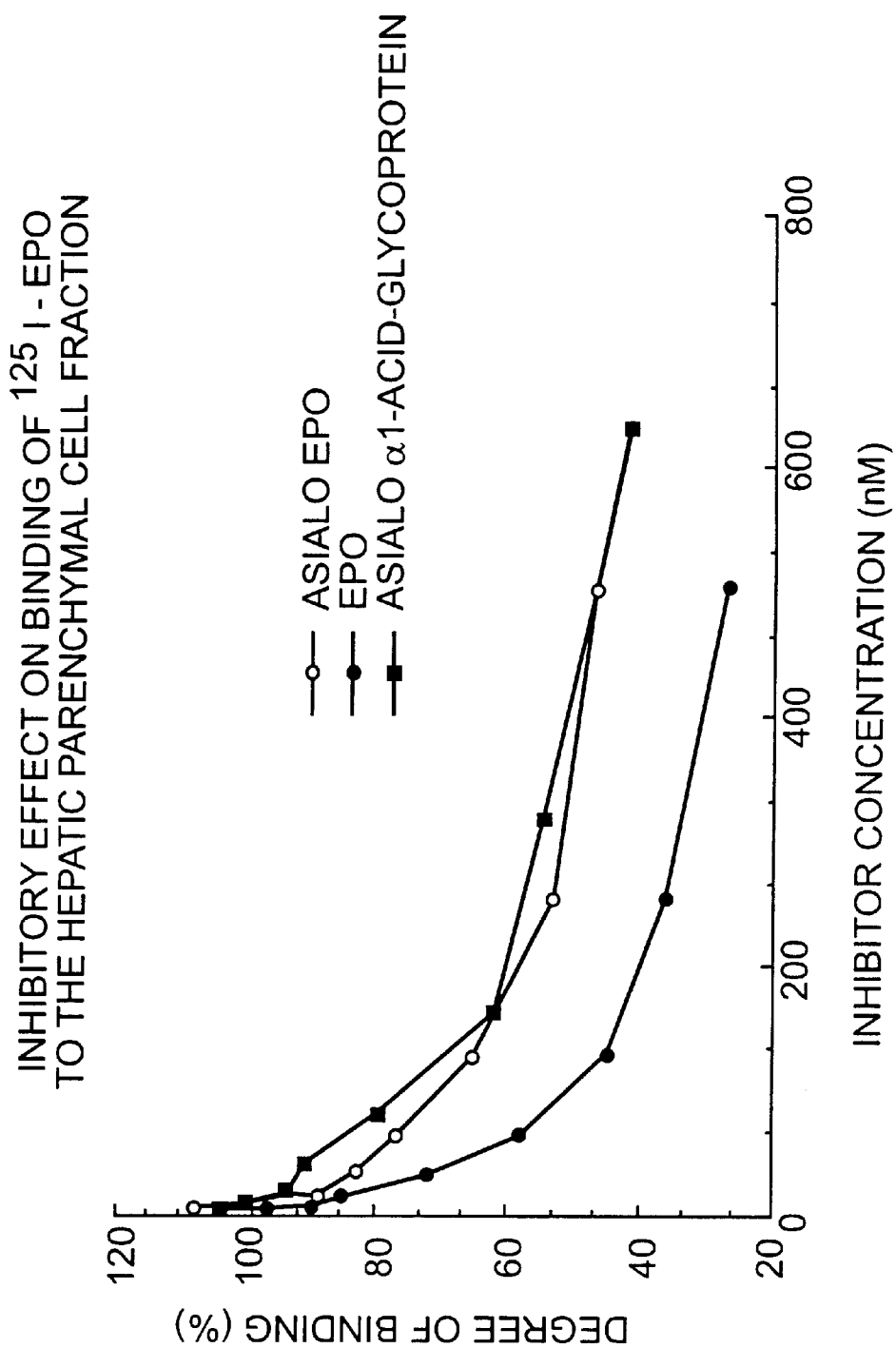
FIG. 2 is a graph where the inhibitory effects of asialo EPO, EPO, and asialo α1-acid-glycoprotein on the binding of $^{125}$I-EPO to a hepatic parenchymal cell (AMLC) fraction were measured.

On the other hand, as a result of measurement of the inhibitory effects of asialo EPO, EPO and asialo α1-acid-glycoprotein on the binding of $^{125}$I-EPO (0.5 nM) to the hepatic parenchymal cell fraction, EPO exhibited the highest inhibitory effect whereas the inhibitory effects of asialo EPO and asialo α1-acid-glycoprotein were partial, as shown in FIG. 2.

These results indicated that there are EPO-specific receptors different from asialo glycoprotein receptors, although some EPO binds to asialoglycoprotein receptors asialorated by the sialidase activity contained in the hepatic parenchymal cell fraction.

[Test Example 2]

Expression of EPO receptors in a human hepatic carcinoma cell line

Expression of EPO receptor mRNA in a human hepatic carcinoma cell line (HepG2 cells) was measured by RT-PCR techniques. The mRNA was prepared from HepG2 cells by a method described by J. E. Badley et al. (Bio Techniques, Vol. 6, No. 2, 114–116 (1988)), and cDNA was prepared from the mRNA by reverse transcription reaction using d(T) 12–18 (Pharmacia Biotech) as primers.

Then, PCR was conducted according to a method described by Y. Nakamura et al. (Science Vol. 257, 21, p. 1138–1141 (1992)) using the following primers:

Sense: TGA GAC ACC CAT GAC GTC TCA

Antisense: TGT CCA GCA CCA GAT AGG TA

Figure 3:
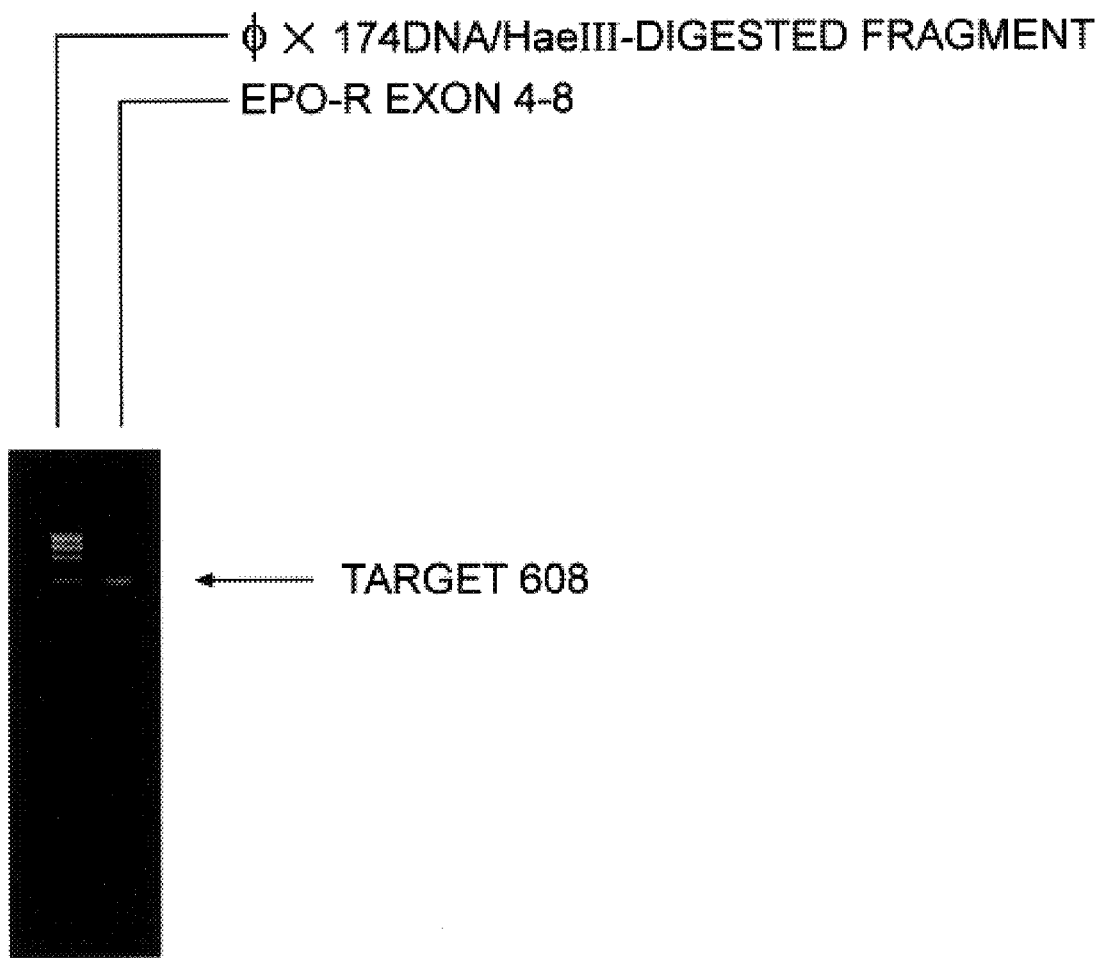
FIG. 3 is a photograph of agarose gel electrophoresis of a PCR product of EPO receptor mRNA expressed in a human hepatic cell strain (HepG2 cells).

As a result of electrophoresis of the resulting PCR product (EPO-R Exon 4-8) on 1.5% agarose gel, an about 608-bp band that is a full-length EPO receptor mRNA was detected as shown in FIG. 3, suggesting that EPO receptors having normal functions are expressed in HepG2 cells.

[Test Example 3]

Action of EPO in releasing iron from hepatic cells

HepG2 cells were cultured in a 24-well cell culture cluster ($2 \times 10^5$ cells/well, MEM containing 10% FCS under 5%

$CO_2$ at 37° C.). Then, $^{59}FeCl_3$ was added at 90,000 cpm and the cells were cultured at 37° C. for 24 hours.

Figure 4:
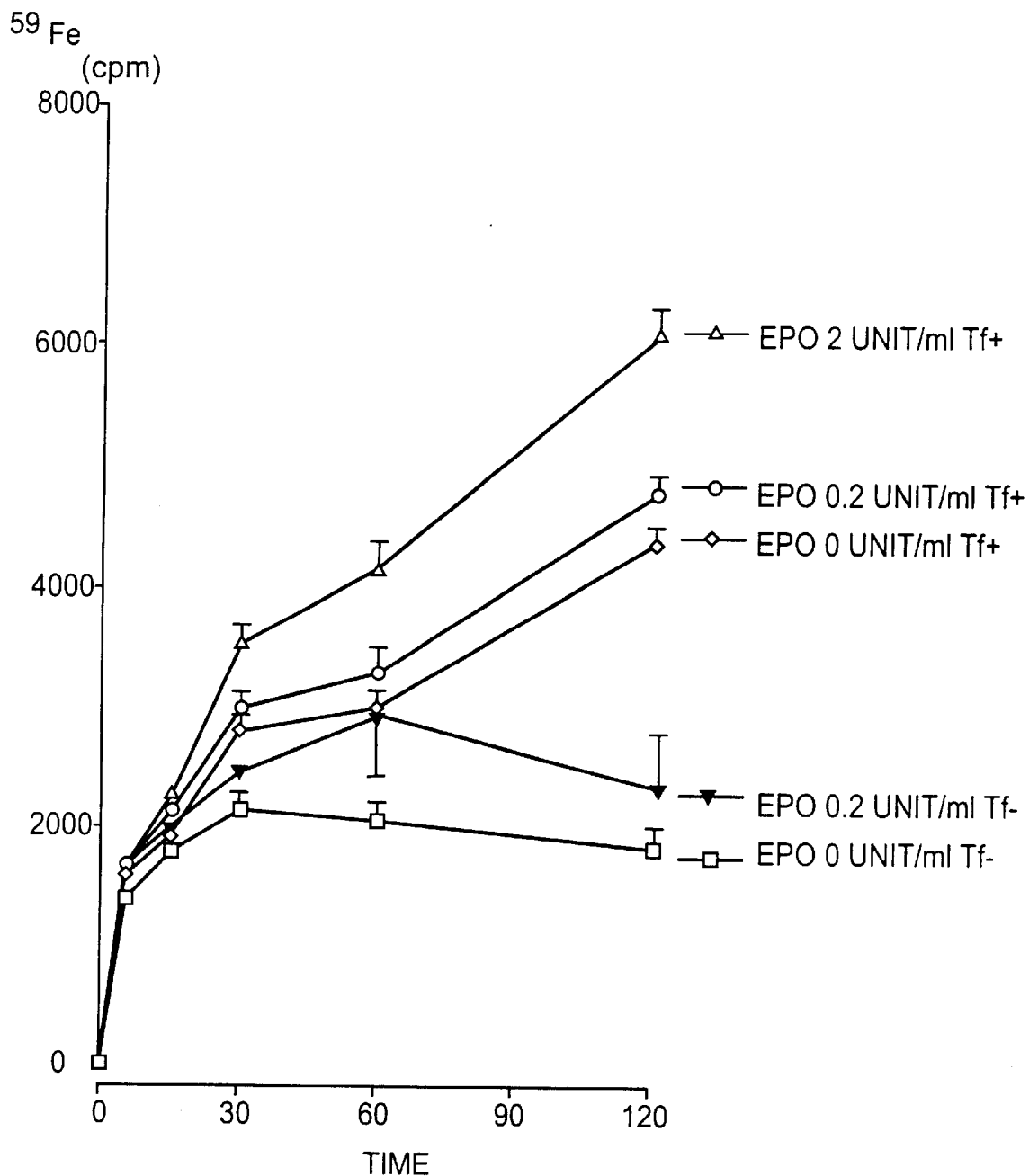
FIG. 4 shows the effect of EPO in releasing iron from a human hepatic carcinoma cell line (HepG2 cells).

After culture was finished, the cells were washed 3 times with FCS-free MEM, and predetermined amounts of EPO (0, 0.2, and 2 units/ml) in the presence or absence of apotransferrin (Tf) (100 µg/ml) were added, and the amount of $^{59}Fe$ released from the hepatocytes to the medium was determined. The results are shown in FIG. 4. FIG. 4 shows that the amount of $^{59}Fe$ released from HepG2 cells increases depending on the concentration of added EPO. It was further seen that the action of EPO in releasing $^{59}Fe$ is enhanced by addition of apotransferrin.

These results indicate that EPO acts directly on hepatic cells to release iron from the cells and that EPO transmits a signal for promoting release of iron via receptors expressed on hepatic cells. It was further indicated that at least transferrin participates in the pathway that releases iron.

[Test Example 4]

Inhibitory effect of EPO on growth of a human hepatic carcinoma cell line

Figure 5:
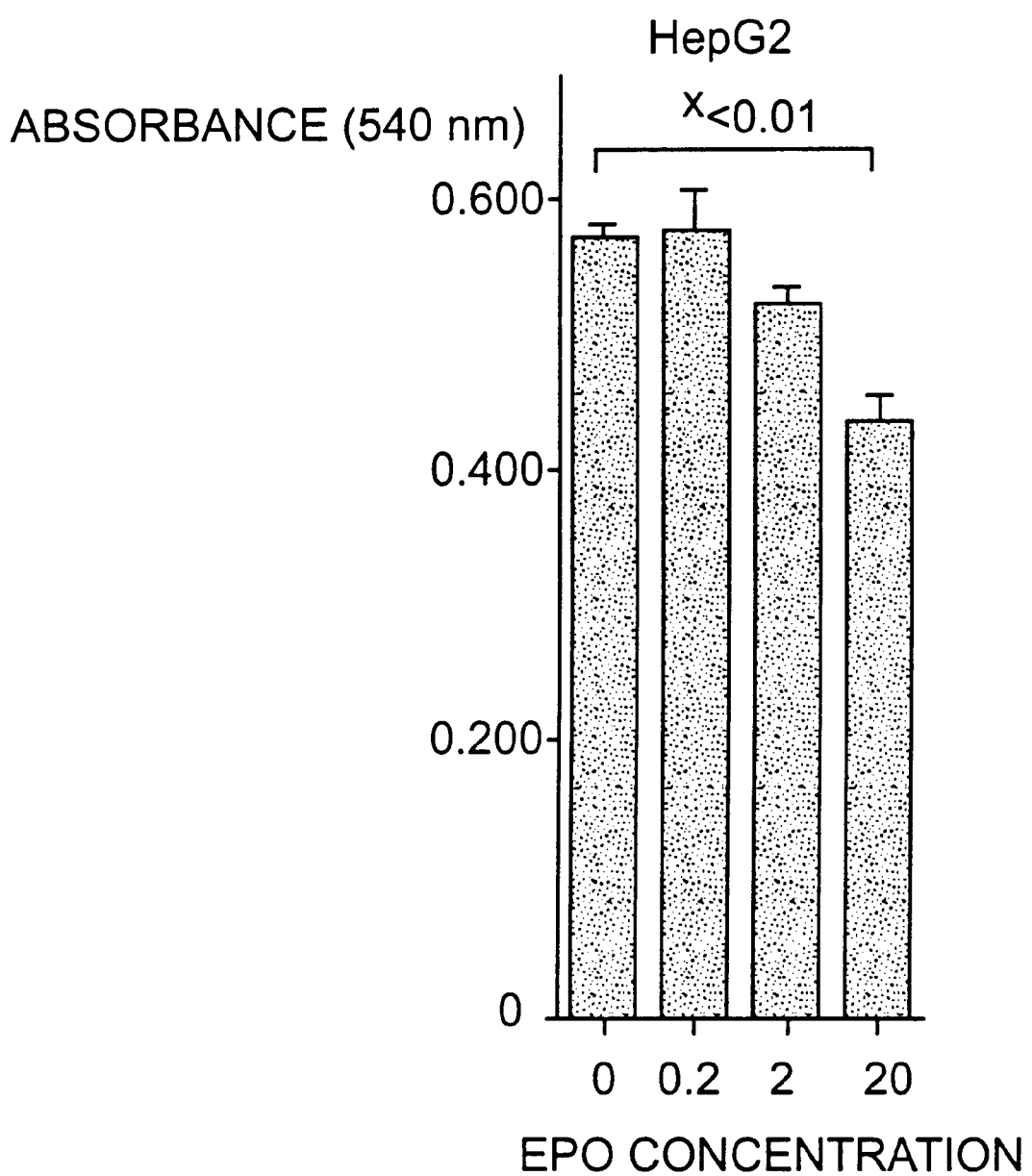
FIG. 5 shows the inhibitory effect of EPO on the growth of a human hepatic carcinoma cell line (HepG2 cells).
Figure 6:
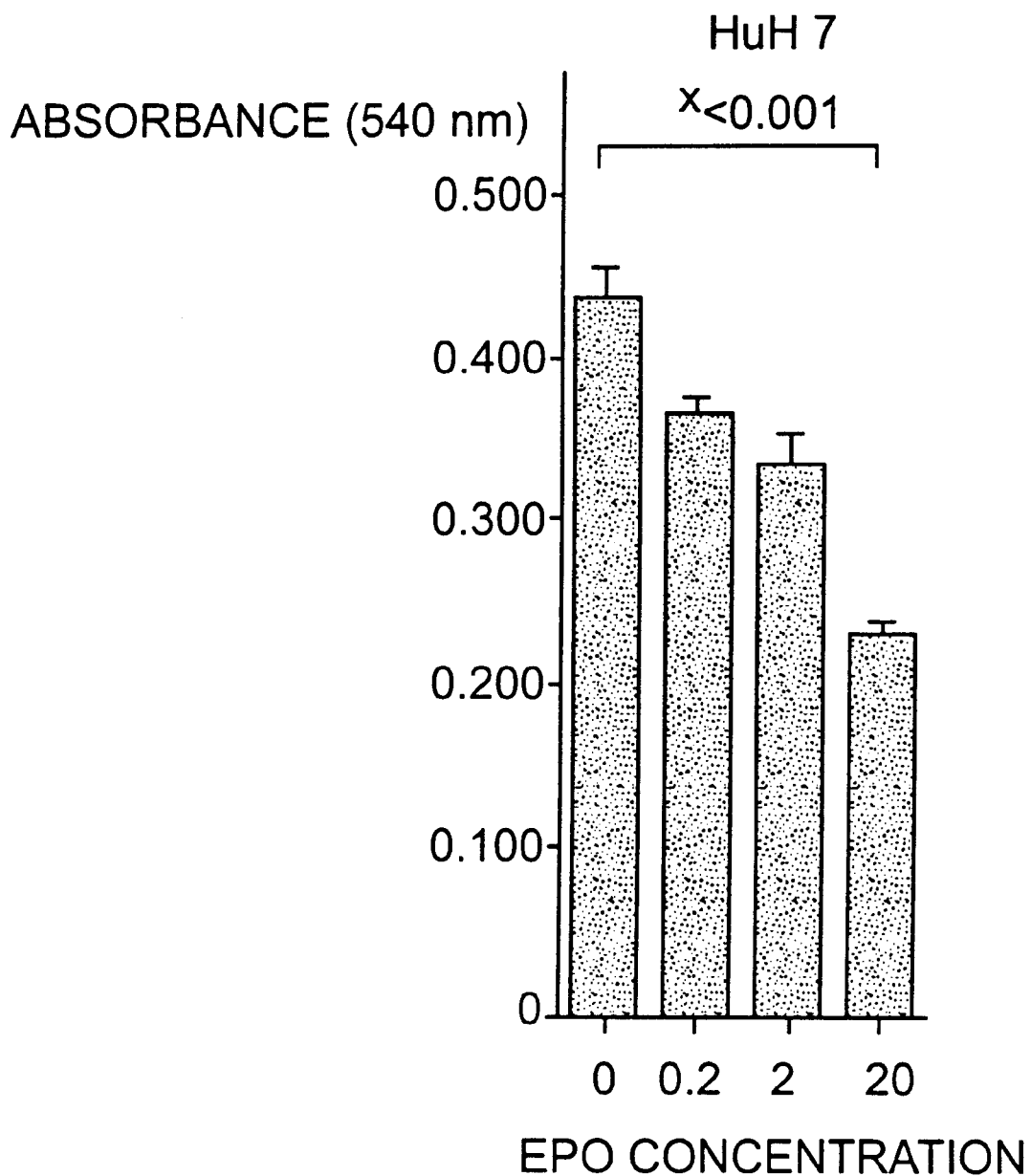
FIG. 6 shows the inhibitory effect of EPO on the growth of a human hepatic carcinoma cell line (HuHG7 cells).

HepG2 cells and HuH7 cells i.e. human hepatic carcinoma cell lines were suspended respectively in MEM and RPMI media containing 2.5% FCS and adjusted to $1\times10^4$ cells/well (96-well dish). The cells were cultured under 5% $CO_2$ at 37° C. for 3 days. EPO was added in the range of 0 to 20 U/ml from the day on which the culture was initiated. After culturing, the number of cells was determined by the MTT method, and the effect of EPO on growth of human hepatic carcinoma cell lines was examined. The results are shown in FIGS. 5 and 6. As can be seen from both the graphs, EPO inhibits growth of HepG2 cells and HuH7 cells.

[Test Example 5]

An interferon-unresponsive patient with chronic hepatitis C, having serum GTP activity fluctuated at higher levels for the last 6 months than the normal range, was subjected weekly to venesection with a volume of 200 ml per venesection for 12 weeks. After every venesection, 24,000 IU EPO was subcutaneously administered.

After the first venesection, serum GTP activity and hemoglobin levels were determined every week and serum ferritin levels were determined every two weeks. Along with the venesection volume, the results are shown in Table 1.

EXAMPLE 1

Production of a Composition for Intravenous Injection 1 mg erythropoietin, 50 mg D-mannitol and 50 mg human serum albumin were aseptically dissolved in 100 ml distilled water for injection and the solution was introduced into a vial (1 ml/vial), lyophilized and sealed. For use, it is dissolved in physiological saline to form a composition for intravenous injection.

INDUSTRIAL APPLICABILITY

According to the present pharmaceutical composition with erythropoietin as an active ingredient, excess iron ions in the liver of a mammal with hepatic diseases can be decreased, so it is effective for treatment of chronic hepatitis, hepatic carcinoma, hepatocirrhosis etc. due to excess iron ions. Further, patient's anemia accompanying venesection can be prevented while excretion of excess iron ions can be promoted by using the venesection therapy in combination with the administration of said pharmaceutical composition.

Furthermore, the pharmaceutical composition of the present invention is administered into a patient with chronic hepatitis C for whom IFN therapy is not effective. The composition improves hepatic functions after which conventional IFN therapy is carried out and exerts a therapeutic effect on the hepatitis.

What is claimed is:

1. A method for the treatment of a hepatic disease, which comprises administering a therapeutically effective amount of a pharmaceutical composition comprising erythropoietin to mammal in need of such treatment.

2. The method for the treatment of a hepatic disease according to claim 1, further comprising a venesection therapy in combination with said treatment.

TABLE 1

|  | 0 week | 1 week | 2 weeks | 3 weeks | 4 weeks | 5 weeks | 6 weeks | 7 weeks | 8 weeks | 9 weeks | 10 weeks | 11 weeks | 12 weeks |
|---|---|---|---|---|---|---|---|---|---|---|---|---|---|
| venesection volume (ml) | 200 | 200 | 200 | 200 | 400 | 400 | 200 | 200 | 0 | 200 | 0 | 200 | — |
| Hb (g/dl) | 14.8 | 14.6 | 14.1 | 15.1 | 14.1 | 13.4 | 12.6 | 13.0 | 12.1 | 11.4 | 11.5 | 11.2 | 10.6 |
| GPT (U) | 84 | 89 | 69 | 73 | 62 | 64 | 56 | 63 | 47 | 23 | 28 | 21 | 26 |
| ferritin (ng/ml) | 293 | — | 79 | — | 35 | — | 22 | — | 19 | — | 19 | — | 14 |

As is evident from Table 1, a significant reduction in serum ferritin levels was observed from 2 weeks after the venesection therapy was initiated, and thereafter, serum GPT activity that is an index of hepatitis at the active stage was reduced. From 9 weeks after the venesection therapy was initiated, the GPT activity was reduced to the normal range in which the activity was maintained thereafter. Hemoglobin levels were maintained at approximately 11.0 g/dl by administration of EPO during the test.

By administration of EPO, 2400 ml blood could be collected by venesection for 12 weeks and excess iron could be removed without causing symptoms of anemia.

3. The method for the treatment of a hepatic disease according to claim 1 or 2, wherein the hepatic disease is chronic hepatitis.

4. The method for the treatment of chronic hepatitis according to claim 3, wherein the chronic hepatitis is due to infection with hepatitis C virus.

5. The method for the treatment of chronic hepatitis according to claim 3, wherein the chronic hepatitis is due to viral hepatitis C or severe hepatitis C.

6. The method for the treatment of a hepatic disease according to claim 1 or 2, wherein the hepatic disease is hepatic carcinoma or hepatocirrhosis.

* * * * *